United States Patent [19]

Burba, III et al.

[11] Patent Number: 5,232,627

[45] Date of Patent: * Aug. 3, 1993

[54] ADDUCTS OF CLAY AND ACTIVATED MIXED METAL OXIDES

[75] Inventors: John L. Burba, III; Arthur E. Read, Jr., both of Lake Jackson, Tex.; Edgar F. Hoy, Midland, Mich.

[73] Assignee: The Dow Chemical Company, Midland, Mich.

[*] Notice: The portion of the term of this patent subsequent to May 12, 2004 has been disclaimed.

[21] Appl. No.: 686,098

[22] Filed: Apr. 16, 1991

Related U.S. Application Data

[63] Continuation-in-part of Ser. No. 166,955, Mar. 11, 1988, Pat. No. 5,015,409, and a continuation-in-part of Ser. No. 526,970, May 16, 1990, Pat. No. 5,094,778, which is a continuation of Ser. No. 282,445, Dec. 9, 1988, abandoned, which is a continuation of Ser. No. 47,800, May 7, 1987, Pat. No. 4,790,954, which is a continuation of Ser. No. 752,326, Jul. 5, 1985, Pat. No. 4,664,843, said Ser. No. 166,955, is a continuation-in-part of Ser. No. 60,133, Jun. 9, 1987, Pat. No. 4,990,268, which is a continuation of Ser. No. 752,325, Jul. 5, 1985, abandoned.

[51] Int. Cl.$^5$ .............. B01J 13/00; C01B 31/16; C01B 33/34; C04B 33/04
[52] U.S. Cl. .................. 252/315.5; 252/71; 252/184; 252/314; 252/174.25; 423/328.2; 428/697; 501/147; 507/140
[58] Field of Search ............ 252/2, 184, 309, 314, 252/315.2, 315.5, 363.5, 28, 71, 174.25; 423/328, 328.2; 501/118, 119, 147; 428/697

[56] References Cited

U.S. PATENT DOCUMENTS

| | | | |
|---|---|---|---|
| 4,454,244 | 6/1984 | Woltermann | 502/208 |
| 4,664,843 | 5/1987 | Burba, III et al. | 252/315.5 |
| 4,790,954 | 12/1988 | Burba, III et al. | 252/315.5 |
| 5,094,778 | 3/1992 | Burba, III et al. | 252/315.2 |

*Primary Examiner*—Richard D. Lovering

[57] ABSTRACT

Adducts of clay, especially of the smectite variety, most especially bentonite, are prepared with an effective amount of at least one activated mixed metal oxide or oxy-hydroxide (AHMMO) formed by dehydrating hydrotalcite or a mixture comprising magnesium oxide and aluminum oxide, or a crystalline mixed metal hydroxide conforming substantially to the formula $$Li_m D_d T(OH)_{(m+2d+3+n.a)} (A^n)_a \cdot xH_2O$$

where m is zero to one, D is a divalent metal, d is from zero to 4, T is a trivalent metal, A represents at least one anion or negative-valence radical of valence n, where n is 1 or more, (m+2d+3+n.a) is equal to or greater than 3, (m+d) is greater than zero, and xH$_2$O represents excess waters of hydration. These adducts are useful, e.g., in drilling muds and in viscosity modification of a wide variety of fluids.

31 Claims, No Drawings

ADDUCTS OF CLAY AND ACTIVATED MIXED METAL OXIDES

CROSS-REFERENCE TO RELATED APPLICATIONS:

This is a continuation-in-part of U.S. patent application Ser. No. 07/526,970 filed May 16, 1990, now U.S. Pat. No. 5,094,778 issued Mar. 10, 1992, which is a continuation application under 37 CFR 1.62 of U.S. patent application Ser. No. 07/282,445 filed Dec. 9, 1988 (now abandoned), which is a continuation application under 37 CFR 1.60 of U.S. patent application Ser. No. 07/047,800 filed May 7, 1987, now U.S. Pat. No. 4,790,954, which is a continuation of U.S. patent Ser. No. 06/752,326 filed Jul. 5, 1985, now U.S. Pat. No. 4,664,843. All of these are incorporated by reference herein in their entirety.

This is also a continuation-in-part of U.S. patent application Ser. No. 07/166,955 filed Mar.-11, 1988, now U.S. Pat. No. 5,015,409, issued May 14, 1991, which is a continuation-in-part of U.S. patent application Ser. No. 07/060,133 filed Jun. 9, 1987, now U.S. Pat. No. 4,990,268, which, itself, is a continuation under 37 CFR 1.60 of U.S. patent application Ser. No. 06/752,325 filed Jul. 5, 1985, now abandoned. All of these are also incorporated by reference herein in their entirety.

FIELD OF THE INVENTION

Activated hydrous mixed metal oxides (AHMMO) are used to form adducts with clays in aqueous media.

BACKGROUND OF THE INVENTION

The above-noted parent applications disclose, inter alia, the making of crystalline layered mixed metal hydroxides (MMOH) and various uses of the MMOH compounds as thickening agents and in their use in the making of clay adducts of the MMOH compounds, with preference shown for the monolayer crystal variety made in a flash coprecipitation process. Whereas the flash coprecipitation process produces monolayer crystals, the sequential method of first forming aqueous aluminum hydroxide to which the other metal(s) is/are intimately added as soluble compound(s) (esp. salts) and then precipitated with OH− ions, produces multi-layer crystals, usually 2-layer or 3-layer, or a mixture of both 2-layer and 3-layer. In some instances the layered MMOH compounds can form stacks of the crystals.

There are some applications in which the above-identified multi-layered crystals of MMOH provide certain advantages of their own, including the formation of adducts with clays. These other advantages include, e.g., the ability of the multi-layered MMOH to be concentrated to a higher degree without reducing their ability to react with clays whereas the monolayer variety of MMOH is very concentration sensitive. Also, the multi-layered MMOH does not require a re-dispersing agent as has been found to be needed with the monolayer variety of MMOH, after it has been at dried at moderate temperatures.

As used herein, the term "activated" (a term often used in the field of minerals and inorganic chemistry) refers to the heating (thermal activation) of metal hydroxides or hydrous metal oxides, sometimes in the presence of $CO_2$, to a temperature high enough to drive off the waters of hydration, leaving the metals as "active" metal oxides or oxy-hydroxides. While one may encounter a chemical method for creating activated metal oxides or oxy-hydroxides, the thermal method would be expected to be the easiest and least expensive method.

The present invention is directed to the making of clay adducts with activated MMOH of the monolayer and the multi-layer variety as well as natural and synthetic hydrotalcites (expressed here simply as $MgO \cdot Al_2O_3$ or $MgAl_2O_4$ since those are the principal components) and other forms of activated mixed metal oxides or mixed metal oxy-hydroxides (all of which are referred to herein as AHMMO). The activated MMOH (hereinafter sometimes referred to as an AHMMO) and other AHMMO compounds, which are arid, are very friable (easily decrepitated), and easily disperse in water as very small crystals, generally of colloidal size.

For example, hydrotalcite is a naturally-occurring mineral (that contains some $CO_2$ in its structure) which, when thermally dehydrated, yields an active magnesium aluminum oxide compound or oxyhydroxide compound. Also for example, magnesium hydroxide and aluminum hydroxide can be combined (especially in the presence of some $CO_2$) and heated to yield mixed metal oxides conforming essentially to the formula $(MgO)x \ Al_2O_3$, where the ratio of Mg/Al can vary over the range of about 0.01/1 to about 6/1, preferably about 0.5/1 to 4/1. Below that range the amount of MgO may not be sufficient to yield a mixed metal oxide which behaves efficiently in the present invention. Above about 4/1, the amount of excess MgO is likely to form a single metal oxide which is present with the mixed metal oxide structure, but as a separate phase.

If heating to ultra high temperatures is done, one may surpass the dehydration temperature at which the activated oxides are produced and can ceramicize or otherwise fuze the oxides into a substantially inert substance. Selection of an appropriate dehydration temperature is within the skill of practitioners of the relevant arts, having learned of this disclosure. Generally, a dehydration temperature in the range of about 400° C. to about 700° C., often about 500° C. to 600° C., is generally sufficient to convert the metal compounds to their activated (dehydrated) oxide or oxy-hydroxide form. Activating other metal compounds (e.g. salts) to obtain the activated oxide form may require more time and/or higher temperature and a more ample supply of oxygen and/or OH−ions.

U.S. Pat. No. 4,748,139 discloses the thermal activation of mixed metal hydroxides at about 500° C.. These activated mixed metal oxides were then made into dense spinel structures at above 1000° C. Examples are shown starting with $Mg(OH)_2$ mixed with $NaAlO_2$ and digested at 105° C. to form a layered magnesium hydroxide/aluminum hydroxide which forms $MgAl_2O_4$ when heated above 500° C.. Also shown is the making of activated layered $CoAl(OH)_5$ plus $Al(OH)_3$ by starting with cobalt hydroxide and aluminum hydroxide. Further shown is the making of activity $CoAl(OH)_5$ by starting with CaO $NaAlO_2$. While this patent teaches the making of some activated mixed metal oxides with are useful in the presently disclosed invention, the patent does not teach the formation of an adduct of clay with the activated mixed metal oxides. It only teaches that the precursor compounds (i.e. prior to heating to activation temperature) can be used in combination with clays for use as drilling fluids the like.

Natural clays and refined natural clays may vary from one mining location to another and the performance obtained with one batch may not exactly match the performance of another batch: the color may not match and the effect on viscosity may not match. The natural clays, and even refined natural clays, may contain impurities which can produce non-uniformity among batches and may create side-reactions with other ingredients in a formulation to which the clay is added. Clays are normally anionic and can react with ingredients which are cationic, such as cationic surfactants used in hair conditioners or in cleansers and the like.

U.S. Pat. No.4,318,732 (Sawyer) discloses that the use of unslaked lime (CaO) or calcium magnesium oxide (CaO.MgO), added as a powder to a ground colloidal clay, produces a resultant liquid product of high yield with acceptable stability, based on the contention that the dry mixture of unslaked lime and ground clay can be stored in paper bags for one year without substantial change by reacting with $CO_2$ from the ambient air. Sawyer discloses that colloidal clays treated with slaked lime ($Ca(OH)_2$) are inherently unstable because of air carbonation (reaction with $CO_2$). Sawyer also teaches that Wyoming bentonite clay is widely used as a gelling clay but it exhibits the disadvantages of not swelling and not developing viscosity in the presence of flocculating cations or in low to medium ionic concentrations. Wyoming bentonite is known to be a sodium bentonite of the smectite family of clays. Sawyer further teaches that attapulgite and sepiolite are unique performers among the clay mineral thickeners in that they can be used to thicken water solutions of salts that contain high concentrations of ionic materials. The examples shown by Sawyer illustrated attapulgite clay.

Both $Ca(OH)_2$ and $Mg(OH)_2$, which are products formed when their respective oxides are wetted with $H_2O$, have a lower limit on pH to remain as dispersions in water. For $Ca(OH)_2$ that lower limit is approximately pH 11.3, and for $Mg(OH)_2$ it is about pH 10. Below these pH values, these hydroxides dissolve and the alkaline earth metal cations, $Ca^{+2}$ and $Mg^{+2}$ are all that can interact with the clay. Drilling fluids are often run in regimes below pH 10 where it would not be possible to have the Sawyer clay/metal hydroxide adduct because the adduct does not form when the metals are in solution and are present only as their cations, which can react with, but are not "adducts" with, the clay.

Mixed metal hydroxides, on the other hand, are stable over a pH range of about 5 to about 14, and the mixed metal hydroxide clay complexes are also stable over a range of about pH 5 to about pH 14. These complexes do not resemble Sawyer's products: the main thing that Sawyer accomplished was the addition of $Ca^{+2}$ and $Mg^{+2}$ ions to the clays in a dry state without adding $Cl^{-}$ ions.

SUMMARY OF THE INVENTION

We have found that activated mono-layered and multi-layered mixed metal hydroxides (MMOH) and other activated hydrous mixed metal oxides, all of which are referred to here as "AHMMO", especially those which are of layered crystalline structures exhibiting cationic surface charges, are beneficially employed as adducts with clay and with other compounds or materials which are anionic.

For purposes of conciseness, the expression "MMOH" will be used in this disclosure to refer to the mixed metal hydroxides which are described in detail below and the expression "AHMMO" will be used in reference to activated forms of the MMOH and activated forms of other hydrous metal oxides. The AHMMO compounds which are made from synthetically produced mixed metal compounds can be of substantially consistent quality and purity. AHMMO compounds made from naturally-occurring minerals, especially hydrotalcites, which can contain small or trace amounts of metal impurities besides the Mg and Al components, are particularly useful in the present invention.

The crystalline mixed metal hydroxides (MMOH) used in the present invention, to create activated mixed metal oxides or oxy-hydroxides, AHMMO, conform substantially to the empirical formula

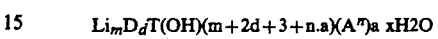

where m is an amount of Li of from zero to one,
where D represents at least one divalent metal cation and d is an amount of from about zero to about 4,
where T represents at least one trivalent metal cation,
where A represents at least one monovalent or polyvalent anion or negative-valence radical,
a is an amount of A ions of valence n, with n.a being an amount of from about zero to about $-3$,
where (m+2d+3+n.a) is equal to or more than 3,
where (m+d) is not zero,
and where $xH_2O$ represents excess waters of hydration, with x being zero or more.

In the above generic empirical formula, "excess waters of hydration" means that there is more water associated with the compound than is needed to supply the amount of hydroxyl ions in the crystal structure. When there is no excess water and x is essentially zero, the compounds, AHMMO, are very fine "activated" crystals having a cationic charge which are found to have a high affinity for forming adducts with anionic compositions such as clay when dispersed in an aqueous liquid.

In the above formula, it should be noted that n, being the valence of the anion, is a negative number: thus n·a is a negative number.

The AHMMO compounds are found to be beneficial as thickeners or viscosity-modifiers for aqueous-based functional products, such as cleansers, commercial products, household products, and personal care products when incorporated therein, as well as forming useful adducts with clay.

In one aspect, the present invention is perceived as being a formulation of the type described having incorporated therein the MMOH or AHMMO compounds.

In another aspect, the present invention is perceived as a means, method, or process for providing viscosity-modifiers or thickeners to the described formulations by incorporating therein the MMOH or AHMMO compounds, especially as adducts with clay.

A further aspect is that AHMMO compounds provide a thickened product which thins readily under even very slight shear, but which rethickens rapidly when the shear is stopped. The gelation rate is perceived as being immediate. Liquid dispersions of clay adducts prepared in accordance with the present invention exhibit the novel rheological behaviour of exhibiting viscosity which is strain dependent. That is, the liquid dispersion is essentially of a gelled consistency in the absence of any strain placed on it, but becomes quite fluid upon application of a strain. It exhibits neither Newtonian activity, nor thixotropic activity, nor dilatant activity, but instead it responds to a strain placed upon it by instantly becoming very fluid, then when the strain is removed it again exhibits a gelled consistency.

In yet another aspect, the present invention is perceived as a beneficial use of the various activated MMOH compounds and other activated hydrous metal oxides.

DETAILED DESCRIPTIONS INCLUDING BEST MODE

Though there are many forms of clays, the clays preferred for use in the present adducts comprise the smectite clays, especially the bentonite-type, and montmorillonite clays. Even though this disclosure is based largely on the bentonite forms of clay, other forms and classes of clay are within the ambit of this invention, such as amorphous clay (e.g. of the allophane group) and crystalline clay (e.g. 2-layer, 3-layer expanding-type, non-expanding type, elongate-type, regular mixed layer type, and chain structure type). For example, a non-exhaustive listing of the clays is as follows:

| bentonite | vermiculite | kaolinite |
| chlorite | halloysite | attapulgite |
| smectite | sepiolite | montmorillonite |
| palygorskite | illite | Fuller's earth |
| saconite | and the like | |

The activated MMOH and AHMMO compounds useful in the present invention are preferably those of the monodispersed, monolayer variety such as described in parent parents U.S. Pat. Nos. 4,664,843 and 4,990,268 identified above. Compounds which are not of the monolayer varieties, but are of the multi-layer varieties, are shown, e.g., in U.S. Pat. Nos. 4,326,961; 4,333,846: 4,347,327: 4,348,295: 4,392,979: 4,446,201: 4,461,714: and 4,477,367. These multi-layered varieties in the activated form can be used in the present invention.

The process, in general, for making the multi-layered varieties of mixed metal hydroxides involves starting with a soluble compound of a tri-valent metal and then reacting that with the desired soluble monovalent metal(s) and/or divalent metal(s) and converting the said compounds with a source of $OH^-$ ions, e.g., $NH_4OH$, at a temperature sufficient to create the multi-layered (generally 2-layer or 3-layer) crystalline mixed metal hydroxide. In contradistinction thereto, the crystalline monolayer mixed metal hydroxides are prepared by combining the desired metal compounds in solution in the desired ratio and then reacting the combination of metal compounds with a source of $OH^-$ ions at an appropriate temperature for producing the mixed metal hydroxide crystals.

Thus, for the most part, the MMOH compounds are prepared by the general process of forming a solution of compounds of the desired metals under appropriate conditions whereby a source of hydroxyl ions, e.g. ammonium hydroxide or caustic, reacts with the soluble metal compounds to produce the layered crystals of mixed metal hydroxides. In some instances, it is often best to avoid having residual ammonia in the product, in which case another hydroxy material, especially NaOH or KOH is used.

The process of using activated MMOH and AHMMO compounds to thicken aqueous-based functional products can be achieved in at least two general ways. One method, in general, involves the activation of the MMOH and AHMMO particles by an electrolyte. In this process, the MMOH and AHMMO is first dispersed by using high shear, sonic waves or other methods known in the art to produce a high degree of dispersion of agglomerated particles. Once the material is dispersed in aqueous or partially aqueous media, a salt (electrolyte) is added either predissolved or dry and mixing/or shearing is continued until a smooth, thickened system is obtained. Other ingredients may be blended into the prethickened material. Often, one or more of the ingredients is a salt and a separate activator is not needed. The salt used for activation can be almost any ionic substance but components containing organic anions or multivalent anions such as $CO_3^{-2}$, $PO_4^{-3}$, $P_3O_{10}^{-5}$ and the like are usually more effective.

The other general method involves interaction with other colloidal particles in such a manner that they are linked together through bridges or bonds formed by the MMOH and AHMMO. In these cases, it can be interpreted as forming an adduct with the other particles. This can produce an "extension" effect. This can happen, for instance, when fumed silica or a clay is also an ingredient and less material is needed for thickening. This can also occur when a normally soluble material is included in the formulation beyond the point of saturation such that very small or colloidal particles are present as crystals or agglomerates In this case, the thickening occurs when the MMOH or AHMMO and other particles are sheared together and agglomerates are broken, exposing fresh faces which react.

As used in this disclosure, the expression "thickener" when used in reference to the effect of the AHMMO additives, means that the apparent viscosity at ambient conditions and at little or no applied shear has been increased by the addition of the AHMMO. The expression "viscosity-modifier" is used herein to refer to the effect obtained by the addition of the AHMMO whether or not the effect on viscosity is evident at ambient conditions or at non-ambient conditions and whether or not the effect is a thickening effect apparent under no-stress conditions or under shear. For example, changing of a Newtonian liquid to a non-Newtonian liquid, or vice-versa, is one form of a viscosity modification. Changing the degree or extent of thixotropicity or dilatancy of a liquid is a form of viscosity modification.

The expression "mixed metal hydroxide" implies that there are at least two- different metals in the hydrous oxide crystals. In the present invention, it is preferred that at least one of the metals is a trivalent metal, along with at least one other metal which can be either, or both, of the divalent or monovalent (Li) varieties, preferably the divalent variety. The amount of the A anion (or negative-valence radical) is that which, with the $OH^{-1}$ ions, substantially satisfies the valence requirements of the cations in the crystalline material. The expression AHMMO can be used for mixed metal varieties or for those which contain only a trivalent metal oxide, especially aluminum, though activated alumina preferably contains at least a very small amount of other metal oxide.

In the above described formula, the trivalent metal cation is preferably Al, Fe, or Ga, and can be mixtures of any of these: Al is most preferred as the trivalent metal.

The divalent metal cation is preferably Mg, Ca, Mn, Fe, Co, Ni. Cu, or Zn and can be mixtures of any of these: Ca or Mg, especially Mg, is most preferred as the divalent metal.

The contents of the numerous formulations that can be thickened or modified by the addition of AHMMO compounds can be varied widely. Generally, the ingredients and levels of the ingredients which are in a given formulation have more to do with a desired effect other than that of thickening or viscosity-modification. The versatility of the AHMMO compounds is beneficial in that it can be added to so many formulations for viscosity purposes without interfering with the other ingredients in their intended purpose. Substitutions, replacements, and/or eliminations of one or more of the components (other than the AHMMO compound) often has little effect on thickening or viscosity-modification.

In the following examples the expression "MAH" is in reference to certain compounds within the generic formula shown above and which conform substantially to the formula $MgAl(OH)_{5-y}Cl_y \cdot xH_2O$ and which are prepared from an aqueous solution containing $MgCl_2$ and $AlCl_3$ as taught, e.g., in parent U.S. Pat. No. 4,664,843. The small amount of $Cl^-$ anion is a residual amount of the $Cl^-$ anion which was in the starting materials.

The following examples are given to illustrate an adduct of clay with AHMMOs: however, the invention is not limited to only the ones illustrated.

EXAMPLE 1:

One gram (1g) of thermally activated MMOH (hydrotalcite) powder which conforms essentially to the empirical formula $Mg_dAlO_a \cdot (OH)_x$ is mixed with 350 g of an aqueous 1.2% sodium bentonite clay dispersion to form an adduct. The mixture is mixed in a Hamilton Beach mixer for 15 minutes*. At this point, 0.5 g of 5 normal NaOH is added with stirring. After 2 minutes, the pH is found to be 10.5. The fluid thickens and rheological properties are determined with a Fann 35 Viscometer**.
Yield Point: 42 lb/100ft$^2$
Plastic Viscosity: 13 centipoise
6 rpm reading: 10 Fann Units
3 rpm reading: 8 Fann Units L6 *Standard procedure for mixing L6 **Standard procedure for measuring rheological properties The above results illustrate an extended bentonite clay very useful as a drilling mud component due to its relatively high yield point and its low viscosity upon application of strain. Because of this the adduct, when used as a drilling mud component, is able to hold drilling solids in suspension even when strain is removed to let the drilling mud come to rest.

EXAMPLE 2:

The above procedure is followed using only the clay dispersion and is tested for its rheological properties.
Yield Point: 2 lb/100ft$^2$
Plastic Viscosity: 3 centipoise
6 rpm reading: 0 Fann Units
3 rpm reading: 0 Fann Units The above results are indicative of a non-extended clay which has poor rheological properties: it flows too easily and does not have enough viscosity to hold drilling solids in suspension.

EXAMPLE 3:

Added 0.15 parts of thermally activated MAH powder to about 350 parts water along with 5 parts bentonite clay to form an adduct. The mixture is mixed in a Hamilton Beach mixer for 15 minutes*. 5N NaOH solution is added, with stirring, to pH 9.0. The fluid thickens and rheological properties are determined with a Fann 35 Viscometer**.
Yield Point: 25 lb/100ft$^2$
Plastic Viscosity: 4 centipoise
6 rpm reading: 15 Fann Units
3 rpm reading: 13 Fann Units L6 *Standard procedure for mixing L6 **Standard procedure for measuring rheological properties The above results illustrate an extended bentonite clay very useful as a drilling mud component due to its relatively high yield point and its low viscosity upon application of strain. Because of this the adduct, when used as a drilling mud component, is able to hold drilling solids in suspension even when strain is removed to let the drilling mud come to rest.

EXAMPLE 4:

The above is repeated except that the pH is brought to 10.5. The fluid thickens and rheological properties are determined with a Fann 35 Viscometer**.
Yield Point: 75 lb/100ft$^2$
Plastic Viscosity: 5 centipoise
6 rpm reading: 26 Fann Units
3 rpm reading: 20 Fann Units L6 *Standard procedure for mixing L6 **Standard procedure for measuring rheological properties The above results illustrate an extended bentonite clay very useful as a drilling mud component due to its relatively high yield point and its low viscosity upon application of strain. Because of this the adduct, when used as a drilling mud component, is able to hold-drilling solids in suspension even when strain is removed to let the drilling mud come to rest.

To the above adduct of pH 10.5 is added sufficient HCl, with stirring to bring the pH to 9.0 and re-tested:
Yield Point: 25 lb/100ft$^2$
Plastic Viscosity: 5 centipoise
6 rpm reading: 26 Fann Units
3 rpm reading: 20 Fann Units Though dropping the pH to 9.0 from the original 10.5 lowers the yield point, the efficacy of the adduct as a drilling component is not destroyed.

EXAMPLE 5:

A sample of mineral hydrotalcite of the general formula $6MgO \cdot Al_2O_3 \cdot CO_2 \cdot 12H_2O$ is heated in a porcelain crucible to a dehydrated state at about 500° C. for several hours. The so-produced AHMMO material is found to be friable. It creates an exotherm, pH increases, and a colloidal dispersion results when placed in water. Into 50 parts of water is place 0.1 part of the AHMMO and mixed with bentonite clay to form and adduct as in the above examples, then tested as shown above.
Yield Point: 50 lb/100ft$^2$
Plastic Viscosity: 12 centipoise
6 rpm reading: 11 Fann Units
3 rpm reading: 7 Fann Units The so-formed adduct is found to be useful as a drilling mud component. The data just above indicates viscosity properties better than clay alone.

EXAMPLE 6:

$MgCl_2$ and sodium aluminate at 1/1 molar ratio are reacted in water, aq. NaOH is added to pH 9.5. An insoluble precipitate forms which is filtered, washed, and dried to dehydration at 500° C. for 2 hours. When dispersed in water a colloidal dispersion forms. The so-formed activated hydrous mixed metal oxide (0.1 parts) is mixed with bentonite (5 parts) to form an adduct in water (to total 350 parts) and tested as above.
Yield Point: 50 lb/100ft$^2$
Plastic Viscosity: 12 centipoise
6 rpm reading: 11 Fann Units
3 rpm reading: 7 Fann Units The data indicate that the adduct is useful as a drilling mud component.

EXAMPLE 7:

Activated mixed metal oxides made in accordance with U.S. Pat. No. 4,748,139 are found to form adducts with clay in accordance with this present invention. The activated mixed metal oxides particularly demonstrated in the patent are:

Mg(OH)$_2$+NaAlO$_2$, digested in water at 105° C. for 24 hours and cooled to allow precipitation. Analyses indicated layered magnesium hydroxide/aluminum hydroxide crystal was formed: it is essentially a synthetic form of hydrotalcite. The MMOH, when heated to above about 500° C. formed an AHMMO.

Co(OH)$_2$+Al(OH)$_3$+NH$_4$OH (as a source of OH-ions to cause precipitation of hydroxides by raising the pH) which was digested to form layered CoAl(OH)$_5$ plus Al(OH)$_3$. Upon heating above about 500° C. an AHMMO is formed.

CaO+NaAlO$_2$+NaOH (only enough to raise pH high enough to solubilize some of the CaO and NaAlO$_2$) to form layered crystalline CaAlO$_4$.

WHAT IS CLAIMED IS:

1. A method for creating an adduct of clay and an activated hydrous mixed metal oxide compound, said method comprising
   mixing together, with stirring, an aqueous dispersion of clay and an amount of activated hydrous mixed metal oxide compound sufficient to thicken the aqueous dispersion of clay or to modify the viscosity of the aqueous dispersion of clay, by the formation of an adduct of the activated hydrous mixed metal oxide compound with the clay, wherein said activated hydrous mixed metal oxide compound comprises at least one compound conforming substantially to the empirical formula

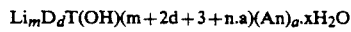

$$\text{Li}_m \text{D}_d \text{T(OH)}_{(m+2d+3+n\cdot a)}(\text{An})_a \cdot x\text{H}_2\text{O}$$

where m is an amount of Li of from zero to one,
   where D represents at least one divalent metal cation and d is an amount of from about zero to about 4,
   where T represents at least one trivalent metal cation,
   where A represents at least one monovalent or polyvalent anion or negative-valence radical,
   a is an amount of A ions of valence n, with n·a being an amount of from about zero to −3,
   where (m+2d+3+n·a) is equal to or more than 3, and where xH$_2$O represents excess waters of hydration, with x being zero or more.

2. The method of claim 1 wherein the clay is at least one selected from the smectite group.

3. The method of claim 3, wherein the clay is bentonite or montmorillonite.

4. The method of claim 1, wherein the activated hydrous mixed metal oxide compound is activated mixed metal hydroxide.

5. The method of claim 1, wherein the activated hydrous mixed metal oxide compound is substantially activated aluminum oxide.

6. The method of claim 1, wherein the activated hydrous mixed metal oxide compound is activated magnesium aluminum oxide.

7. The method of claim 1, wherein the activated hydrous mixed metal oxide compound is magnesium aluminum oxy-hydroxide.

8. The method of claim 1, wherein the activated hydroxy mixed metal oxide compound is magnesium aluminum oxide wherein the ratio of Mg/Al is in the range of about 0.01/1 to about 6/1.

9. The method of claim 1, wherein the activated hydrous mixed metal oxide compound is magnesium aluminum oxide wherein the ratio of Mg/Al is about 0.01/1 to about 4/1.

10. The method of claim 1 wherein the D metal is at least one selected from the group consisting of Mg, Ca, Mn, Fe, Co, Ni, Cu, and Zn 11. The method of claim 1 wherein the D metal is at least one of the group consisting of Ca and Mg.

12. The method of claim 1 wherein the T metal is at least one selected from the group consisting of Al, Fe, and Ga.

13. The method of claim 1 wherein the T metal is Al.

14. The method of claim 1 wherein m is zero, d is one, and n·a is an amount in the range of zero to one.

15. The method of claim 1 wherein A represents at least one inorganic anion or negative-valence radical.

16. The method of claim 1 wherein A represents a hydrophilic organic negative-valence group.

17. The method of claim 1 wherein the A anion represents at least one of the group consisting of hydroxyl, halide, sulfate, nitrate, phosphate, carbonate, glycolate, lignosulfate, and polycarboxylic or negative-valence radicals.

18. The method of claim 1, wherein the activated hydrous mixed metal hydroxide compound is MgAl(OH)$_{(t+n\cdot a)}$(A$^n$)$_a$·xH$_2$O), where n·a is an amount of from zero to one, where A is an anion other than OH− and xH$_2$O is an indefinite amount of excess waters of hydration.

19. The method of claim 18 wherein the A anion is a halide.

20. The method of claim 18 wherein the A anion is chloride.

21. The method of claim 1, wherein the activated hydrous often hydrous mixed metal oxide is of the crystalline, monodispersed, monolayer variety.

22. A composition comprising an adduct of clay and an activated hydrous mixed metal oxide compound of an effective amount of at least one crystalline compound conforming essentially to the formula

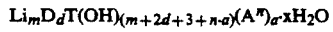

$$\text{Li}_m \text{D}_d \text{T(OH)}_{(m+2d+3+n\cdot a)}(\text{A}^n)_a \cdot x\text{H}_2\text{O}$$

where m is from zero to one,
   D is a divalent metal and d is an amount of from about 0 to about 4,
   T is at least one trivalent metal,
   A represents at least one monovalent or polyvalent anion or negative-valence radical,
   a is an amount of A ions of valence n, with n·a being an amount of from about zero to about −3,
   (m+2d+3+n·a) is equal to or more of than 3,
   and xH$_2$O represents excess waters of hydration, with x being zero or more.

23. The composition of claim 22 wherein the D metal is Mg and the T metal is Al.

24. The composition of claim 22 wherein the activated hydrous mixed metal oxide compound conforms essentially to the formula $$MgAl(OH)_{(5+n\cdot a)}(A^n)_a \cdot xH_2O$$

where A is chloride and n·a is an amount of from zero to minus one and x is zero or more.

25. The composition of claim 22 wherein the clay is bentonite.

26. The composition of claim 22 wherein the clay is bentonite, a smectite, or a montmorillonite.

27. An aqueous dispersion of an adduct of activated hydrotalcite and clay.

28. The aqueous dispersion of claim 27 wherein the weight percent of clay is in the range of about 0.1 to about 10 and the weight percent of the activated hydrotalcite is in the range of about 0.0005 to about 3.

29. The aqueous dispersion of claim 27 wherein the weight percent of clay is in the range of about 0.2 to about 5 and the weight percent of the activated hydrotalcite is in the range of about 0.005 to about 0.8.

30. The aqueous dispersion of claim 27 wherein the clay is bentonite.

31. The process of making the dispersion of claim 27, said process comprising dispersing activated hydrotalcite in water and mixing it with colloidal clay.

* * * * *

UNITED STATES PATENT AND TRADEMARK OFFICE
CERTIFICATE OF CORRECTION

PATENT NO. : 5,232,627
DATED : August 3, 1993
INVENTOR(S) : John L. Burba, III et al.

It is certified that error appears in the above-indentified patent and that said Letters Patent is hereby corrected as shown below:

Column 10, line 40, in the formula "t" should read --5--.

Column 10, line 11, "droxy" should read --drous--.

Column 11, line 17, "bentonite," should read --a bentonite,--.

Signed and Sealed this

Tenth Day of May, 1994

*Attest:*

BRUCE LEHMAN

*Attesting Officer*     *Commissioner of Patents and Trademarks*